(12) United States Patent
Boussignac

(10) Patent No.: US 6,363,935 B1
(45) Date of Patent: Apr. 2, 2002

(54) DEVICE FOR RESPIRATORY ASSISTANCE

(76) Inventor: Georges Boussignac, 1, Avenue de Provence, 92160 Antony (FR)

( * ) Notice: Subject to any disclaimer, the term of this patent is extended or adjusted under 35 U.S.C. 154(b) by 0 days.

(21) Appl. No.: 09/387,790

(22) Filed: Sep. 1, 1999

(30) Foreign Application Priority Data

Sep. 3, 1998 (FR) .......................................... 98 11027

(51) Int. Cl.$^7$ ............................................ A61M 16/00
(52) U.S. Cl. ............................. 128/207.14; 128/207.15
(58) Field of Search ....................... 128/207.14–207.16, 128/911, 912, 200.24, 200.26, 204.25, 204.18, 204.22, 204.23; 604/527

(56) References Cited

U.S. PATENT DOCUMENTS

| | | | | |
|---|---|---|---|---|
| 3,881,480 A | * | 5/1975 | Lafourcade | 128/145.8 |
| 4,022,219 A | * | 5/1977 | Basta | 128/351 |
| 4,207,884 A | * | 6/1980 | Isaacson | 128/200.24 |
| 4,270,530 A | * | 6/1981 | Baum et al. | 128/204.25 |
| 4,558,708 A | * | 12/1985 | Labuda et al. | 128/207.14 |
| 4,825,862 A | | 5/1989 | Sato et al. | |
| 5,291,882 A | * | 3/1994 | Makhoul et al. | 128/207.14 |
| 5,452,715 A | * | 9/1995 | Boussignac | 128/207.15 |
| 5,513,628 A | * | 5/1996 | Coles et al. | 128/200.26 |
| 5,538,002 A | * | 7/1996 | Boussignac et al. | 128/207.16 |
| 5,544,648 A | * | 8/1996 | Fischer, Jr. | 128/207.14 |
| 5,598,840 A | * | 2/1997 | Iund et al. | 128/207.14 |
| 5,715,815 A | * | 2/1998 | Lorenzen et al. | 128/207.14 |
| 6,152,132 A | * | 11/2000 | Psaros | 128/204.25 |
| 6,173,711 B1 | * | 1/2001 | Rutton | 128/204.26 |
| 6,273,087 B1 | * | 8/2001 | Boussignac et al. | 128/204.22 |

FOREIGN PATENT DOCUMENTS

| | | |
|---|---|---|
| EP | 0390684 | 3/1990 |
| WO | WO 95/28193 | 10/1995 |
| WO | WO 97/18003 | 5/1997 |

* cited by examiner

*Primary Examiner*—John G. Weiss
*Assistant Examiner*—Teena Mitchell
(74) *Attorney, Agent, or Firm*—Fisher, Christen & Sabol

(57) ABSTRACT

The present invention relates to a device for respiratory assistance comprising a tube (4) which is provided with at least one auxiliary channel (8) for insufflating a jet of respirable gas into the respiratory system of a patient, and means (14b) for deflecting said jet of gas in the direction of the inside of the main channel (5) of said tube (4).

According to the invention, the device comprises a ring (36) arranged in the main channel (5) downstream of said means of deflection (14b) and said ring (36) encloses the oblong pressure zone (18) by at least partially closing off the peripheral space (37) of said main channel situated between the inner wall (15) thereof and said oblong pressure zone (18).

7 Claims, 2 Drawing Sheets

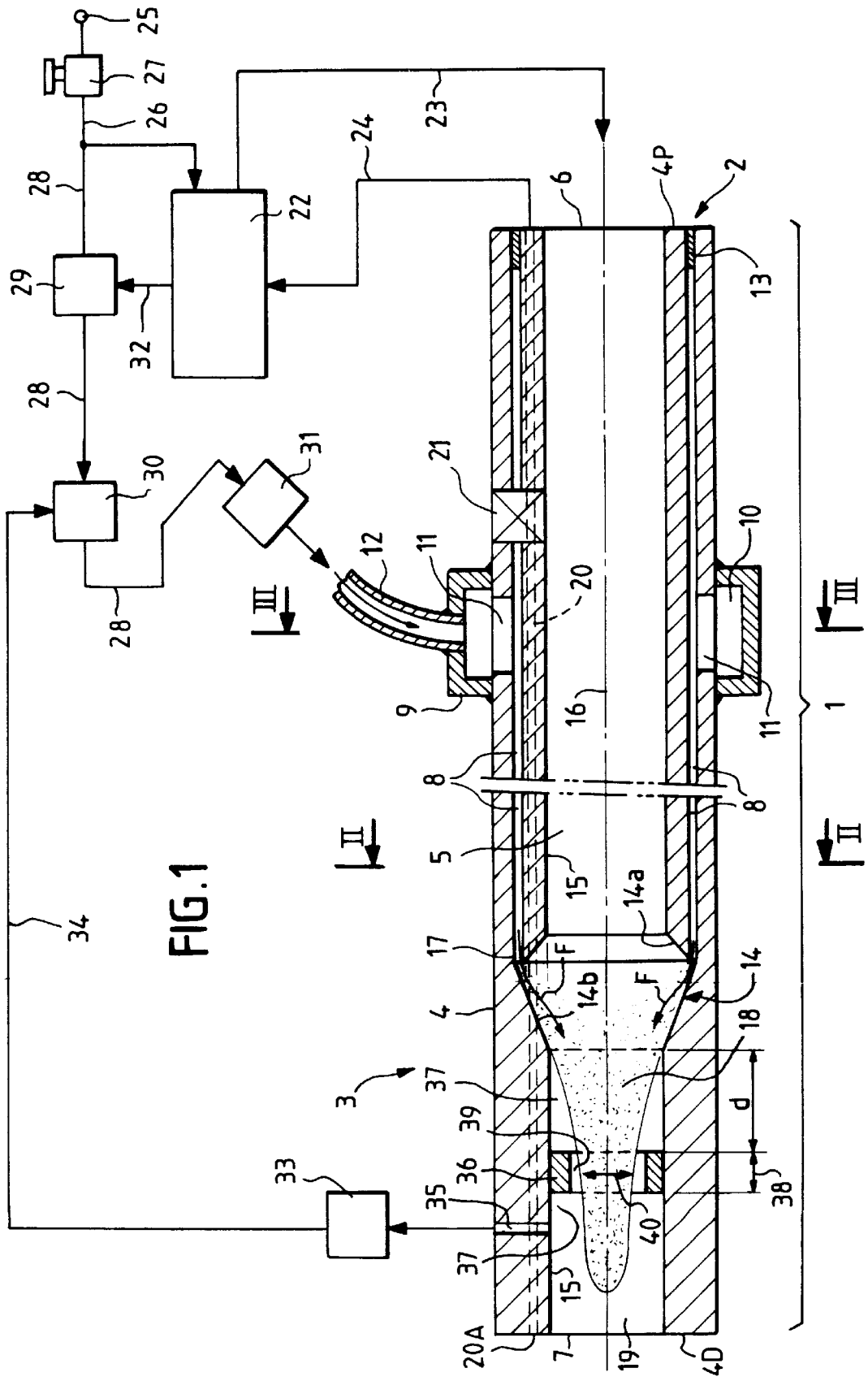

DEVICE FOR RESPIRATORY ASSISTANCE

The subject of the present invention is a device for respiratory assistance which can be used on patients in whom spontaneous respiration is absent or inadequate, whether or not said patients are placed under artificial respiration.

Various devices are known, such as masks and oral, nasal, endotracheal and tracheotomy probes or cannulas, which are intended to form the junction between an artificial respiration and/or anesthesia apparatus and the respiratory system of a patient. These devices, essentially in the form of tubes, can, depending on the circumstances, include immobilizing means such as flanges or collars in the vicinity of the proximal end for holding them on the mouth or nose of the patient, or alternatively inflatable balloons in the vicinity of the distal end for holding them by friction in the trachea.

The known devices have significant disadvantages. Thus, for example, when a tube of a known type is disconnected from the artificial respirator and the patient needs oxygen-enriched air, it is necessary to introduce into said tube a probe which is connected to an oxygen source. Moreover, in cases of inadequate spontaneous respiration, the patient must necessarily remain connected to the respirator until spontaneous respiration has been completely re-established.

Thus to overcome these disadvantages, it has already been proposed, for example in document EP-A-0 390 684, to provide devices for respiratory assistance which, in addition to the main channel formed by the tube, comprise at least one auxiliary channel, for example formed in the wall of said tube, permitting injection of a jet of respirable gas (oxygen, air or air/oxygen mixture) intended to ventilate the patient, these auxiliary channels opening into the main channel in the vicinity of the distal end of the latter.

To prevent the jets of respirable gas from striking directly against the mucosa of the patient under ventilation, the kinetic energy of these jets risking trauma to said mucosa, it is provided, in these latter devices, that at least the distal end of said auxiliary channels opening into the main channel is parallel to the latter and, opposite the distal orifice of each auxiliary channel, there are means for deflecting said jets of respirable ventilation gas toward the inside of said main channel.

Thus, the jets of respirable gas passing through said auxiliary channels are deflected toward the axis of the main channel when they penetrate into the latter. Experimental measures have shown that downstream of said means of deflection, inside said main channel, a pressure zone of oblong shape is formed starting at the outlets of said auxiliary channels into the main channel and extending in the axial direction along the axis of said main channel, with gradual reduction of its cross section, so as to occupy only In the central part thereof, while downstream of said high pressure zone, the pressure of said jets of respirable gas falls and the jets of gas emerge at low pressure through the distal orifice of the tube. Experience has also shown that downstream of the distal outlet of the tube, the pressure is low and is maintained constant throughout the entire respiratory space. This pressure is dependent on the flow rate of respirable gas in the auxiliary channels. Consequently, with the respiratory assistance device according to the above document, it is possible for example to deliver oxygen or an air/oxygen mixture directly into a patient's lungs, at the level of the carina, and thus suppress the dead space which exists in the other known probes and which is about one third of the total respiratory volume for an adult and about half for premature babies. Suppression of this dead space corresponds to an increase in performance of the respiratory cycle of more than 25% in all patient cases and of nearly 50% in certain cases.

The device in document EP-A-0 390 684 is thus particularly advantageous. However, it has the disadvantage of requiring a source of respirable gas at high pressure (several bar) to supply said auxiliary channels. Such a source may not be available and it may be expedient, for reasons of safety, to be able to use sources of respirable gas at low pressure (for example below one bar).

Thus, the object of the present invention is to improve the device in document EP-A-0 390 684 so that it can function with a source of respirable gas at low pressure.

To this end, according to the invention, the device for respiratory assistance comprising a tube which forms a main channel and which is intended to be connected via its distal end to the respiratory tract of a patient so that said main channel connects the respiratory system of said patient to the outside, said device moreover comprising at least one auxiliary channel connected at its proximal end to a source of respirable gas so as to insufflate a jet of such a respirable gas into said respiratory system, and whose distal end opens into said main channel in the vicinity of the distal end of the latter, means for deflecting said jet of respirable ventilation gas in the direction of the inside of said main channel being provided opposite the distal orifice of said auxiliary channel so that, downstream of said means of deflection, inside said main channel, a pressure zone of oblong shape is formed starting at said distal orifice and extending in the distal direction along the axis of said main channel, with gradual reduction of its cross section as it moves away from the inner wall of said main channel so as to occupy only the central part of the latter, is distinguished by the fact that it comprises a ring arranged in said main channel downstream of said means of deflection (in relation to said jet of respirable gas), and by the fact that said ring encloses said oblong pressure zone by at least partially closing off the peripheral space of said main channel situated between said inner wall thereof and said oblong pressure zone.

The Applicant found that by means of this ring it was possible to use a source of respirable gas at lower pressure while obtaining an oblong pressure zone of identical pressure, or alternatively to obtain an oblong pressure zone at higher pressure using a source of respirable gas of identical pressure. It was therefore as if said ring, by peripherally restricting said main channel and leaving only the central part of the cross section thereof free, permitted better utilization of the pressure of said source of respirable gas for forming said oblong pressure zone.

The Applicant found by experimentation that it was advantageous for the distance separating said ring from said means of deflection to be approximately equal to the diameter of the distal part of said main channel. Said ring could be fixed inside said main channel or even form an integral part of said tube. However, in order to be able to optimize the pressure gain on the source of respirable gas, it is preferable for this distance to be adjustable. For the same purpose, it is also advantageous for the internal diameter of said ring to be adjustable in order to adapt the orifice of the latter to the central section of said pressure zone to the best possible extent. It is then expedient to provide a set of interchangeable rings, of different internal diameters, which can be introduced and displaced by sliding inside the distal end of said tube. Alternatively, it is possible to use rings in the form of inflatable cuffs in such a way as to be able easily to modify their internal diameter.

It will also be noted that by virtue of the present invention it is particularly easy to provide a humidifier in the conduit connecting the source of respirable gas to the auxiliary channel. Indeed, the present invention makes it possible to lower the pressure of the jet of respirable gas in said conduit to a level permitting good humidification thereof. It is thus possible to prevent the patient's mucosa from drying out.

When the device according to the invention advantageously includes a plurality of auxiliary channels, it is advantageous for at least some of them to be supplied jointly with respirable gas. Such joint supply of said channels can be achieved by way of a distribution ring which is coaxial with said tube. Moreover, said auxiliary channels which are not jointly supplied can be used for introducing additional gaseous products such as medicinal products.

Thus, it will be seen that the device according to the invention permits, in complete safety:

humidification of the insufflated respirable gas,
long-term intubation of the respiratory assistance without drying,
injection of medicines or anesthetics during respiratory assistance,
dynamic measurement of pressures, since it suffices to provide auxiliary channels to which appropriate probes are associated,
establishment of a microflow of respirable gas in the auxiliary channels to prevent obstruction of said channels by mucus,
an increase in the volume exchanged, since the pressure is automatically limited and there is no risk of crushing of the pulmonary capillaries,
for the same quantity of oxygen exchanged, a decrease in the amount of oxygen in the mixture, which accordingly reduces the secondary effects of the assistance,
the possibility of using respirators which are less expensive then the current respirators.

It is also advantageous, particularly for safety reasons, for the device according to the present invention to have a controllable valve mounted in the conduit connecting the source of respirable gas to said auxiliary channel and for said valve to be controlled by a sensor detecting the patient's exhalation. Thus, said valve can be closed during the patient's exhalation, so that this exhalation is free through said tube, the jets of respirable gas and said central oblong pressure zone then being suppressed. Said sensor preferably detects the patient's exhalation downstream of said ring, that is to say in the direction away from said means of deflection.

The figures in the attached drawing will show clearly how the invention can be achieved. In these figures, identical references designate like elements.

FIG. 1 is a diagrammatic and partial view, in enlarged axial section, of an embodiment of the device of the invention.

Figure 3:
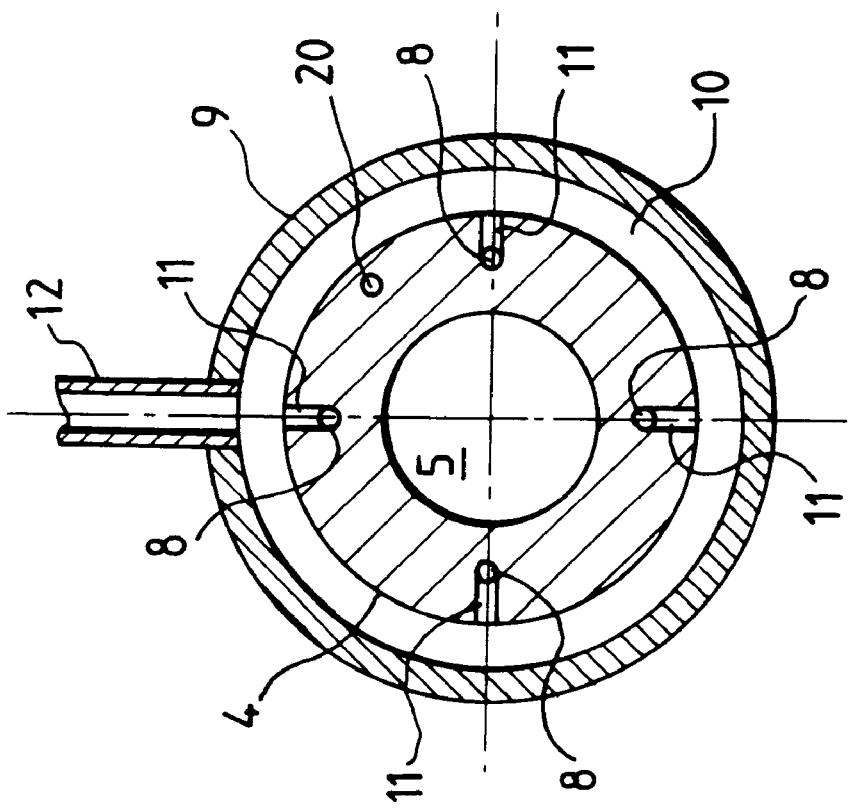
FIGS. 2 and 3 are cross sections along lines II—II and III—III, respectively, in FIG. 1.

FIG. 1 represents, diagrammatically and on a large scale, only the proximal end 2 and distal end 3 of an embodiment 1 of the device according to the invention. This embodiment can constitute, for example, an oronasal endotracheal probe with or without balloon, a pediatric endotracheal probe, a probe for gas monitoring, an endobronchial probe, a nasopharyngeal probe, an anatomical intubation probe for children, a Cole neonatal probe, a Gedel cannula probe, a nasal probe for oxygen therapy, a nasal or bucconasal mask or a nasal balloon for treatment of sleep apnea.

The device 1 includes a tube 4 which is flexible or pre-shaped (to adapt to the morphology of the patient) and which delimits a main channel 5 opening out via the orifice 6 at the proximal end 2 and via the orifice 7 at the distal end 3.

Thus, the main channel 5 is capable of ensuring passage between the orifices 6 and 7, one of which (orifice 7) is intended to be located within the airways of a patient, while the other (orifice 6) is intended to be located outside said patient. This orifice 6 can open to the ambient air, and in this case the patient can inhale fresh air and exhale vitiated air through the main channel 5. As is explained below, it is also possible to connect the orifice 6 to a source of respirable gas under pressure and to provide a system of unidirectional valves, so that the patient inhales the respirable gas from said source via said main channel 5 and exhales the vitiated gas to the ambient air, again via this main channel.

The diameter of the main channel 5 is of the order of a few millimeters. Satisfactory trials have been conducted with diameters of 3 mm, 7 mm, 8 mm and 12 mm.

Moreover, auxiliary channels 8 are formed within the thickness of the wall of the tube 4, said auxiliary channels 8 extending over almost the entire length of the main channel and being intended to be connected to a source of respirable gas under pressure, as is described below.

The connection to the source of respirable gas under pressure can be effected by means of a ring 9, surrounding the tube 4 in a leaktight manner toward the proximal end 2 and delimiting a sealed annular chamber 10 around said tube. The auxiliary channels 8 are brought into communication with the chamber 10 by means of local cutouts 11 in the wall of the tube 4, and said chamber 10 is connected to said source of respirable gas via a conduit 12. Of course, the proximal ends of the channels 8 are closed off, for example by stoppers 13 introduced from the proximal end face 4P of the tube 4.

The auxiliary channels 8 have a smaller diameter than that of the main channel 5. The diameter of the auxiliary channels 8 is preferably less than 1 mm and is advantageously of the order of 400 to 800 microns. At the distal end, the auxiliary channels 8 open into a recess 14 in the inner wall 15 of the tube 4. The recess 14 is annular and centered on the axis 16 of the distal end 3. It includes a face 14a which is substantially transverse or slightly inclined in such a way as to constitute a widening of the main channel 5 into which said auxiliary channels 8 open via their orifices 17, as well as a face 14b following the face 14a and converging in the direction of the axis 16.

Thus, when the auxiliary channels 8 are supplied with respirable gas under pressure by way of the elements 9 to 12, the corresponding gaseous jets impact the inclined face 14b, which deflects them in the direction of the axis 16 (arrows F in FIG. 1), generating in the distal end 3 of the main channel 5 a pressure zone 18 of oblong shape starting at said distal orifices 17 and extending in the direction of the distal orifice 7 along the axis 16 of said distal end 3. The cross section of the pressure zone 18 decreases progressively from the recess 14 toward the distal orifice 7, said pressure zone 18 moving progressively away from the inner wall 15 of the tube 4 so as to occupy only the central part of the distal end 3 of the latter. Downstream of the pressure zone 18, the deflected jets of respirable gas generate in the vicinity of the axis 16 an underpressure zone 19 favoring the gas circulation inside the main channel 5 from the proximal orifice toward the distal orifice. This promotes the patient's inhalation.

At least one supplementary channel 20 is provided within the thickness of the tube 4 and opens out at 20A in the distal end face 4D of the tube 4 and serves as a pressure tap.

For safety reasons, a calibrated exhaust valve 21 can be provided in the proximal end 2 of the tube 4. Thus, in the event of an accidental overpressure occurring in the main channel 5, gas escapes to outside the patient, via the wall of the tube 4, in order to eliminate this overpressure instantaneously.

Figure 2:
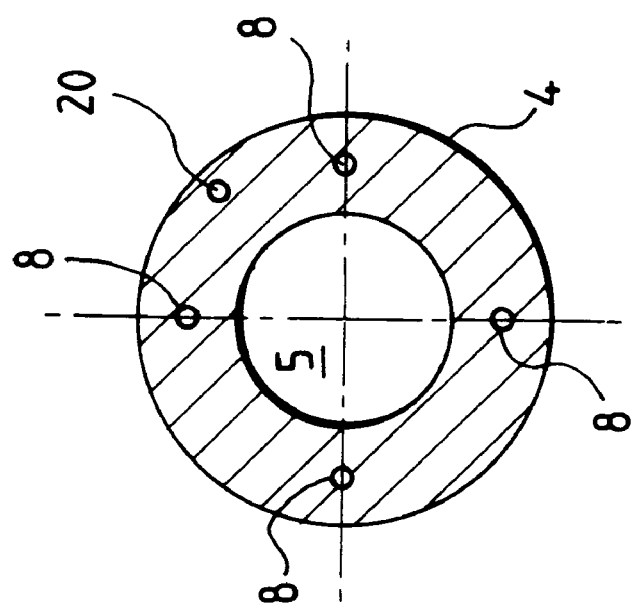

As is shown in FIGS. 2 and 3, the auxiliary channels 8 are arranged regularly around the axis of the tube 4. Their number is variable depending on the applications (adult or child), but is generally between three and nine. Moreover, at least one of the auxiliary channels 8 can be specialized to deliver a medical fluid.

The tube 4 of the device according to the invention can be made of any material already used in respiratory probes, for example polyvinyl chloride, with an optional coating of silicone or steel permitting high-pressure injections.

Of course, the dimensions of the device according to the invention can vary greatly, essentially depending on the mode of fitting of the tube and the size of the patient, who can be an adult, a child, an infant or a premature baby.

The device 1 moreover comprises a supply and control device 22 which is connected to the orifice 6 of the proximal end 2 of the tube 4 via a connection 23 and to the supplementary channel 20 via a connection 24, respectively.

The supply and control device 22 is supplied with respirable gas under pressure via a source 25, to which it is connected via a conduit 26 on which an adjustable pressure reducer/flowmeter 27 is mounted.

The outlet of the pressure reducer/flowmeter 27 is connected to the conduit 12 via a branch conduit 28 on which there are mounted in series a first controllable valve 29, a second controllable valve 30 and a humidifier 31.

The controllable valve 29 is controlled by the supply and control device 22 by way of a connection 32.

The controllable valve 30 is controlled by a detector 33 by way of a connection 34. The detector 33 is a pressure sensor or a flow rate sensor which is able to detect the changes from inhalation to exhalation in the patient's breathing. The measurement tap 35 of the detector 33 is situated in the vicinity of the distal orifice 7.

Arranged in the distal end 3, between said measurement tap 35 and the inclined deflection face 14b, there is a ring 36 surrounding the central pressure zone 18 and occupying locally at least in part the annular peripheral space 37 situated between said central pressure zone 18 and the inner wall 15 of the distal end 3 of the channel 5.

By means of such a ring 36, as has been explained above, the pressure of the source of respirable gas 25 needed for obtaining the pressure zone 18 can be lowered.

As a general rule, the distance d between the ring 36 and the inclined deflection face 14b is close to the diameter of the distal part of the main channel 5.

However, in order to obtain the necessary optimum reduction in pressure of the source 25, it is advantageous for this distance d to be adjustable, as is illustrated by the double arrow 38. It is also advantageous, for the same reason, for the diameter of the central opening 39 of the ring 36 to be adjustable, as is illustrated by the double arrow 40. This double adjustment can be achieved by virtue of a set of several interchangeable rings 36 which can be chosen to be mounted slidably in the distal end of the main channel 5. The ring 36 can alternatively consist of an inflatable cuff, whose internal diameter can be varied by inflation.

The modes of operation of the device 1 according to the invention are the following:

in the artificial respiration mode, the supply and control device 22, on the one hand, controls the valve 29 to close by way of the connection 33, so that the conduit 12 is not supplied with gas, and, on the other hand, conveys respirable gas into the tube 4 by way of the connection 23. This device 22 includes means (not shown) by which it is possible to regulate the pressure and flow rate of respirable gas which it receives from the conduit 26 and which it conveys to the tube 4. If an overpressure occurs in the respiratory tract of the patient, it is detected and transmitted, via the supplementary channel 20 and the connection 24, to the device 22 which stops operating. Moreover, if this overpressure exceeds the calibration threshold of the calibrated valve 21—for example because the supplementary channel 20 is obstructed by mucus and has not been able to transmit the overpressure information to the device 22—this valve 21 opens and the proximal channel 5 is connected to the atmosphere;

in the respiratory assistance mode, the supply and control device 22 cuts off the connection 23 in order to bring the orifice 6 into communication with the atmosphere and controls the valve 29 via the connection 33 so that it conveys to the patient continuous or pulsed jets of respirable gas by way of the valve 30, the humidifier 31 and the auxiliary channels 8.

With a source pressure 25 lower than in the prior art device, the pressure zone 18 and the underpressure zone 19 thus form permitting easy ventilation of the patient. The latter can then inhale deeply and freely. When, after an inhalation, the patient begins to exhale, the detector 33 detects this start of exhalation and controls the valve 30 to close. The jets of respirable gas, the pressure zone 18 and the underpressure zone 19 thus disappear and the patient can exhale freely through the main channel 5. If, during ventilation, an overpressure occurs in the respiratory tract of the patient, as was described above, this overpressure is detected and transmitted via the supplementary channel 20, so that the device 22 closes the valve 29 and ventilation is stopped.

Thus, from what has been described above, it will be evident that the invention permits, with a moderate pressure source, efficient and reliable humidified respiratory assistance, with almost complete disappearance of the dead space inherent to the known probes.

What is claimed is:

1. A device for respiratory assistance comprising:

a tube (4) forming a main channel (5) with an inner wall (15) and having an axis (16), a proximal end (2) and a distal end (3), said tube (4) being intended to be connected via said distal end (3) to a respiratory system of a patient so that said main channel (5) connects such a respiratory system to the outer environment of said patient;

at least one auxiliary channel (8) having a proximal end and a distal end and being connected at said proximal end of said auxiliary channel to a source of respirable gas (25) via a conduit (28) so as to insufflate a jet of such a respirable gas into such a respiratory system, said distal end of said auxiliary channel having a distal orifice (17) opening into said main channel (5), in the vicinity of said distal end of said main channel (5);

means (14b) for deflecting said jet of respirable gas in the direction of said axis (16) of said main channel (5), said deflecting means (14b) being provided opposite said distal orifice (17) of said auxiliary channel (8) so that a pressure zone (18) of oblong shape is formed inside said main channel (5) downstream of said deflection means (14b) in relation to said jet of respirable gas, said pressure zone (18) having a cross section around said axis (16) and starting at said distal orifice (17) and extending in the direction of said distal end of said main channel (5) along said axis (16) with gradual reduction of said cross section by progressively moving away from said inner wall (15) of said main channel (5) so as to occupy only a central part of said main channel (5) around said axis (16) and to be surrounded by a peripheral space (37) of said main channel delimited between said inner wall (15) and said oblong pressure zone (18); and a ring (36) arranged in said main channel (5) downstream of said deflecting means (14*b*) in relation to said jet of respirable gas, said ring (36) reducing in diameter said main channel (5) and surrounding said oblong pressure zone (18) by at least partially closing off said peripheral space (37) of said main channel situated between said inner wall (15) and said oblong pressure zone (18).

2. The device as claimed in claim 1, wherein the distance (d) separating said ring (36) from said deflecting means (14*b*) is approximately equal to the diameter of said distal end of said main channel (5).

3. The device as claimed in claim 1, wherein the distance (d) separating said ring (36) from said deflecting means (14*b*) is adjustable.

4. The device as claimed in claim 1, wherein the internal diameter of said ring (36) is adjustable.

5. The device as claimed in claim 1, comprising a humidifier (31) in the conduit (28) connecting the source of respirable gas (25) to said auxiliary channel (8).

6. The device as claimed in claim 1, comprising a controllable valve (30) mounted in said conduit (28) connecting the source of respirable gas (25) to said auxiliary channel (8), wherein said controllable valve (30) is controlled by a sensor (33) detecting said patient's exhalation.

7. The device as claimed in claim 1, wherein said sensor (33) detects the patient's exhalation downstream of said ring (36) in relation to said jet of respirable gas, that is to say in the direction away from said deflecting means (14*b*).

* * * * *